(12) United States Patent
Sachdeva et al.

(10) Patent No.: US 6,318,995 B1
(45) Date of Patent: Nov. 20, 2001

(54) METHOD AND APPARATUS FOR BONDING A BRACKET TO A TOOTH

(75) Inventors: Rohit Sachdeva, Plano, TX (US); Rudger Rubbert, Berlin (DE); Thomas Weise, Berlin (DE); Friedrich Riemeirer, Berlin (DE)

(73) Assignee: DraMetrix, Inc., Dallas, TX (US)

( * ) Notice: Subject to any disclaimer, the term of this patent is extended or adjusted under 35 U.S.C. 154(b) by 0 days.

(21) Appl. No.: 09/560,129

(22) Filed: Apr. 28, 2000

Related U.S. Application Data

(63) Continuation-in-part of application No. 09/552,189, filed on Apr. 19, 2000.

(51) Int. Cl.⁷ .................................................. A61C 3/00
(52) U.S. Cl. ............................................................ 433/24
(58) Field of Search ........................... 433/8, 9, 18, 24, 433/223

(56) References Cited

U.S. PATENT DOCUMENTS

| | | |
|---|---|---|
| Re. 35,169 | 3/1996 | Lemchen et al. .................... 433/24 |
| 3,738,005 | 6/1973 | Cohen ................................ 32/14 B |
| 4,575,805 | 3/1986 | Moermann et al. . |
| 5,011,405 | 4/1991 | Lemchen . |
| 5,238,404 | 8/1993 | Andreiko . |
| 5,368,478 | 11/1994 | Andreiko et al. . |
| 5,395,238 | 3/1995 | Andreiko et al. . |
| 5,431,562 | 7/1995 | Andreiko et al. . |
| 5,447,432 | 9/1995 | Andreiko et al. . |
| 5,454,717 | 10/1995 | Andreiko et al. . |
| 5,456,600 | 10/1995 | Andreiko et al. . |
| 5,464,349 | 11/1995 | Andreiko et al. . |
| 5,474,448 | 12/1995 | Andreiko et al. . |
| 5,518,397 | 5/1996 | Andreiko et al. . |
| 5,533,895 | 7/1996 | Andreiko et al. . |
| 5,542,842 | 8/1996 | Andreiko et al. . |
| 5,618,176 | 4/1997 | Andreiko et al. . |
| 5,879,158 | * 3/1999 | Doyle et al. ........................ 433/24 |
| 5,975,893 | 11/1999 | Chishti et al. ...................... 433/6 |
| 6,068,482 | 5/2000 | Snow ................................ 433/223 |
| 6,099,314 | 8/2000 | Kopelman et al. ................ 433/213 |
| 6,217,325 | 4/2001 | Chishti et al. ..................... 433/24 |
| 6,227,850 | 5/2001 | Chishti et al. ..................... 433/24 |

FOREIGN PATENT DOCUMENTS

| | | |
|---|---|---|
| 44 45 552 | 6/1995 | (DE) . |
| 196 36 354 | 3/1998 | (DE) . |
| 196 38 727 | 3/1998 | (DE) . |
| 196 38 758 | 3/1998 | (DE) . |

OTHER PUBLICATIONS

Syrinx, Bending Robot Brochure, undated.
Syrinx, Orthotherm Brochure, undated.
Syrinx, 3D Scanner Brochure, undated.

* cited by examiner

*Primary Examiner*—Nicholas D. Lucchesi
(74) *Attorney, Agent, or Firm*—McDonnell Boehnen Hulbert & Berghoff

(57) ABSTRACT

A method and apparatus for bonding a bracket to a tooth includes processing that begins by obtaining a digital model of a desired bracket placement on a tooth. The processing continues by scanning actual placement of the bracket on the tooth to produce digital information of the actual placement and generating a digital model of the actual placement. The processing continues by comparing the digital model of the desired bracket placement with the digital model of the actual placement. When the digital model of the desired bracket placement substantially matches the digital model of the actual placement, enabling bonding of the bracket to the tooth.

25 Claims, 5 Drawing Sheets

METHOD AND APPARATUS FOR BONDING A BRACKET TO A TOOTH

CROSS REFERENCE TO RELATED APPLICATION

This is a continuation-in-part of Ser. No. 09/552,189 filed Apr. 19, 2000.

TECHNICAL FIELD OF THE INVENTION

This invention relates generally to the practice of orthodontics and in particular to a method and apparatus for generating an orthodontic template for placing orthodontic apparatus.

BACKGROUND OF THE INVENTION

Orthodontics is known to be the practice of manipulating a patient's teeth to provide better function and appearance. In general, brackets are bonded to a patient's teeth and coupled together with an arch wire. The combination of the brackets and wire provide a force on the teeth causing them to move. Once the teeth move to a desired location and are held in place for a certain period of time, the body adapts bone and tissue to maintain the teeth in the desired location. To further assist in retaining the teeth in the desired location, the patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his or her expertise to place the brackets and/or bands on the teeth and then manually bends (i.e., shape) the arch wire such that a force is asserted on the teeth to reposition the teeth into the desired physical orthodontic structure. As the teeth move towards the desired location, the orthodontist makes continual judgments as to the progress in the treatment, the next step in the treatment (e.g., new bends in the arch wire, repositioning or replacing brackets, is headgear required, etc.) and the success of the previous step.

In general, the orthodontist makes manual adjustments to the arch wire and/or replaces or repositions brackets based on his or her own expert opinion. Unfortunately, in the oral environment, it is impossible, using human sight, to accurately develop a three-dimensional mental image of an orthodontic structure due to the limitations of human site and the physical structure of a human mouth. In addition, it is humanly impossible to accurately estimate three-dimensional wire bends (with an accuracy within a few degrees and to manually apply such bends to a wire). Further it is humanly impossible to determine an ideal bracket location to achieve the desired orthodontic structure based on mental images. It is also extremely difficult to manually place brackets in the estimated ideal location, to control bonding agent thickness, ligation forces, manufacturing tolerances, and biological changes. Accordingly, orthodontic treatment is an iterative process, which varies depending on diagnostics, biology, therapeutic approach and appliance system. As such, orthodontic treatment typically requires multiple wire changes, with the type, success, and speed of treatment being very much dependent on the orthodontist's motor skills and diagnostic expertise. As a result of multiple wire changes, patient discomfort is increased as well as treatment costs. As one would expect, the quality of care varies greatly from orthodontist to orthodontist, as does the time to treat a patient.

As described, the practice of orthodontics is very much an art, relying on the expert opinion and judgment of the orthodontist. In an effort to shift the practice of orthodontics from an art to a science, many innovations have been developed. For example, U.S. Pat. No. 5,518,397 issued to Andreiko, et. al, provides a method of forming an orthodontic brace. Such a method includes obtaining a model of the teeth of a patient's mouth and a prescription of desired positioning of such teeth. The two-dimensional contour of the teeth of the patient's mouth is determined from the model. Calculations of the contour and the desired positioning of the patient's teeth are then made to determine the geometry (e.g. grooves or slots) to be provided in the brackets. Custom brackets including a special geometry have been created for receiving an arch wire to form an orthodontic brace system. Such geometry is intended to provide for the disposition of the arched wire on the bracket in a progressive curvature of a horizontal plane and a substantially linear configuration in a vertical plane. The geometry of the bracket is altered, (e.g., by cutting grooves into the bracket at individual positions and angles and with particular depth) and in accordance with such calculations of the geometry of the patient's teeth. In such a system, the brackets are customized to provide three-dimensional movement of the teeth once the wire, which has a two-dimensional shape, (i.e., linear shape in the vertical plane and curvature in the horizontal plane) is applied to the brackets.

Unfortunately, the current innovations to change the practice of orthodontics from an art to a science have only made limited progress. This is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of a millimeter or less and an angle of a few degrees or less) can cause a different force system (i.e., magnitude of movement and direction of movement) than the desired force system to be applied to the teeth. As such, the tooth will not be repositioned to the desired location.

To assist in the accurate placement of brackets on a tooth, a jig may be utilized. On such jig is disclosed in U.S. Pat. No. 5,368,478 issued to Andreiko, et. al which provides a method for forming jigs for custom placement of orthodontic appliances on teeth. In general, the '478 patent teaches that each jig is provided with a surface conforming to the contour of the tooth to which they are to be mounted. Another surface of the jig engages the bracket to hold it in the proper position and orientation for mounting to the tooth and spaced in relation to the contour surface to precisely locate the jig on the tooth. The jigs are particularly useful in positioning brackets of custom appliances desired to the individual anatomy of the patient and requiring custom positions of the brackets on the teeth. While the '478 patent discloses a method for forming a jig, such jig utilization still keeps the bracket as the focal point of the orthodontic treatment and provides no feedback mechanism regarding actual placement of the bracket. Further, the '478 patent does not allow for variables associated with tooth movement such as static, dynamic, or psychosocial mechanical and/or biological changes.

Therefore, a need exists for a method and apparatus for providing feedback when placing brackets on teeth to insure proper placement.

BRIEF DESCRIPTIONS OF THE DRAWINGS

DETAILED DESCRIPTION OF A PREFERRED EMBODIMENT

Generally, the present invention provides a method and apparatus for bonding a bracket to a tooth by constructing a digital orthodontic template coupled with a validation approach. Such a method and apparatus includes processing that begins by obtaining a digital model of a desired bracket placement on a tooth. The processing continues by scanning actual placement of the bracket on the tooth to produce digital information of the actual placement and generating a digital model of the actual placement. The processing continues by comparing the digital model of the desired bracket placement with the digital model of the actual placement. When the digital model of the desired bracket placement substantially matches the digital model of the actual placement, enabling bonding of the bracket to the tooth. With such a method and apparatus, an iterative approach for verifing bracket placement may be obtained prior to adhering the bracket to the tooth using a feedback loop that allows an orthodontist to optimally locate orthodontic appliances. As such, the present invention provides a mechanism for further insuring that the use of a jig or other placement techniques accurately places the bracket utilizing a feedback system prior to adhering the bracket to the tooth.

Figure 1:
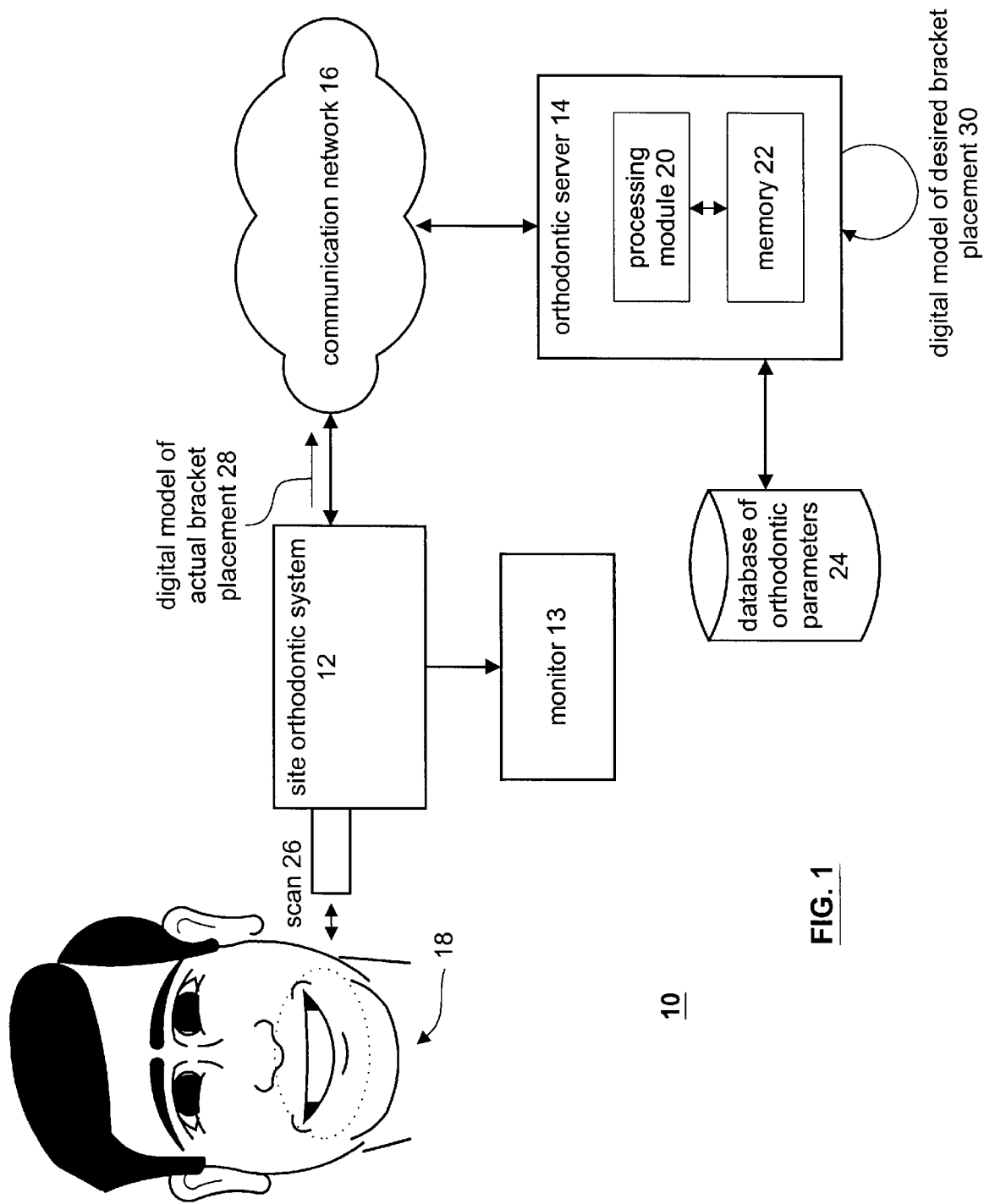
FIG. 1 illustrates a schematic block diagram of an orthodontic system in accordance with a preferred embodiment of the present invention.

The present invention can be more fully described with reference to FIGS. 1 through 5. FIG. 1 illustrates a schematic block diagram of an orthodontic servicing system 10 that includes a site orthodontic system 12, an orthodontic server 14, a communication network 16 and a database of orthodontic parameters 24. In operation, the site orthodontic system 12 scans 26 the patient's 18 orthodontic structure (i.e., teeth, gums, lips, upper and lower arches, and/or other facial features) with the brackets temporarily installed. Note that the scanning may be done by ultrasound, laser, light refraction, and/or video imaging in two-dimensional or three-dimensional mode based on the therapeutic needs. The site orthodontic system converts the scanned images of the orthodontic structure of the patient to produce a digital model of the actual bracket placement 28. The orthodontic server 14 receives the digital model of the actual bracket placement 28 via communication network 16. The communication network 16 may be a direct connect, the internet, local area network, wide area network and/or any device that enables the transference of digital information from one computing type system to another. Note that a specific embodiment of three-dimensional scanning is described in patent application having a Ser. No. 09/560,129, filed before the United States Patent Office on Apr. 28, 2000, and is hereby incorporated herein by reference.

The orthodontic server 14 includes a processing module 20 and memory 22. The processing module 20 may be a single processing device or a plurality of processing devices. Such a processing device may be a microprocessor, microcomputer, microcontroller, digital signal processor, central processing unit, state machine, logic circuitry, and/or any other device that manipulates signals (e.g., analog and/or digital) based on operational instructions. The memory 22 may be a single memory device or a plurality of memory devices. Such a memory device may be read-only memory, random access memory, floppy disk memory, hard drive memory, system memory, flash memory, and/or any device that stores digital information. Note that when the processing module 20 implements one or more of its functions via a state machine or logic circuitry, the memory storing the corresponding operational instructions is embedded within the circuitry comprising the state machine and/or logic circuitry.

The orthodontic server 14 generates a three-dimensional digital model of the desired bracket placement 30 in accordance with the teachings of co-pending patent application, which is hereby incorporated herein by reference, entitled "Method and Apparatus for Determining Tooth Movement in accordance with an Ideal Orthodontic Structure" filed on Nov. 30, 1999 having a Ser. No. of 09/451,609 and with co-pending patent application, which is hereby incorporated herein by reference, entitled "Method and Apparatus for Designing an Orthodontic Apparatus to Provide Tooth Movement" filed on Nov. 30, 1999 having a Ser. No. of 09/451,564. For a more detailed discussion of the site orthodontic system 12, the orthodontic server 14 and the database of orthodontic parameters 24 refer to co-pending patent applications, which are hereby incorporated herein by reference, entitled "Method and Apparatus for Determining and Monitoring Orthodontic Treatment" filed Nov. 30, 1999 having a Ser. No. of 09/451,637, "Method and Apparatus for Treating an Orthodontic Patient" filed Nov. 30, 1999 having a Ser. No. of 09/451,560, and "Method and Apparatus for Site Treatment of an Orthodontic Patient" filed on Nov. 30, 1999 and having a Ser. No. of 09/452,038.

Figure 2:
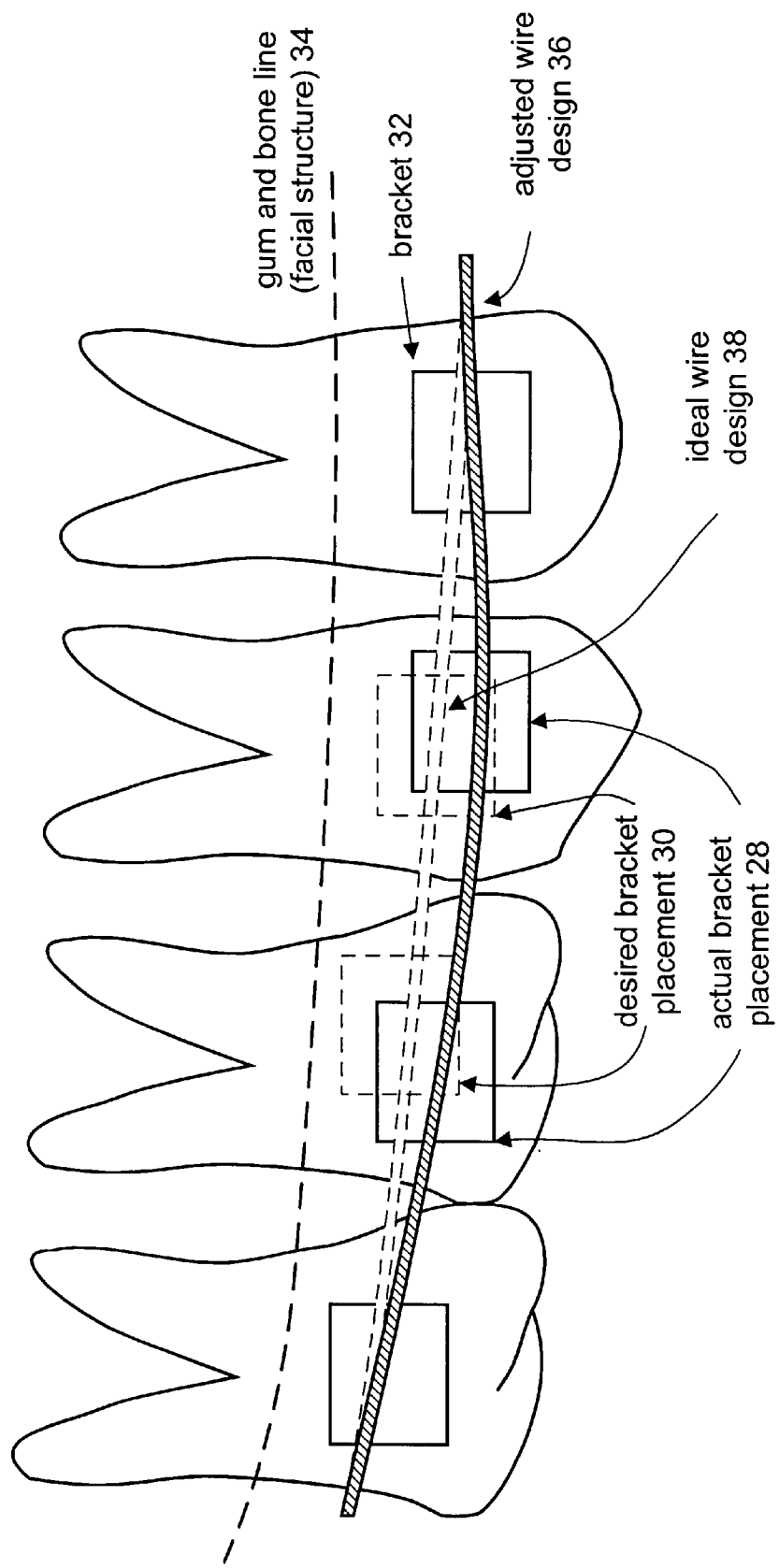
FIG. 2 illustrates a graphical representation of an actual bracket placement versus ideal bracket placement in accordance with a preferred embodiment of the present invention.

FIG. 2 illustrates a graphical representation of the actual placement of brackets and arch wire on a patient's teeth. Note that the wire will not he installed until the brackets have been placed and secured. The illustration also includes a desired bracket placement 30 in comparison to the actual bracket placement 28. As shown, even with the use of a jig or other positioning mechanisms, the actual bracket placement 28 may not correspond to the desired bracket placement 30. By placing the brackets on the tooth and, prior to permanently securing the brackets to the teeth, the actual bracket placement is scanned. The scanned information is then converted to a digital model that may be utilized to compare the actual bracket placement with the desired bracket placement. If an error exists, as shown in FIG. 2, the practitioner may re-orientate the bracket placement such that the actual bracket placement coincides with the desired bracket placement. Once the bracket has been placed, the arch wire 36 or 38 is installed to produce the desired force system on the teeth. As shown, the orthodontic apparatus includes the bracket and arch wire and is mounted on the teeth below the gum and bone line (facial structure) 34. Note that the term bracket, as used herein, includes a bracket, a band, head gear tube, or any device used to mount onto a patient's tooth for reception of a displacement apparatus such as an arch wire, rubber band, and/or head gear.

Figure 3:
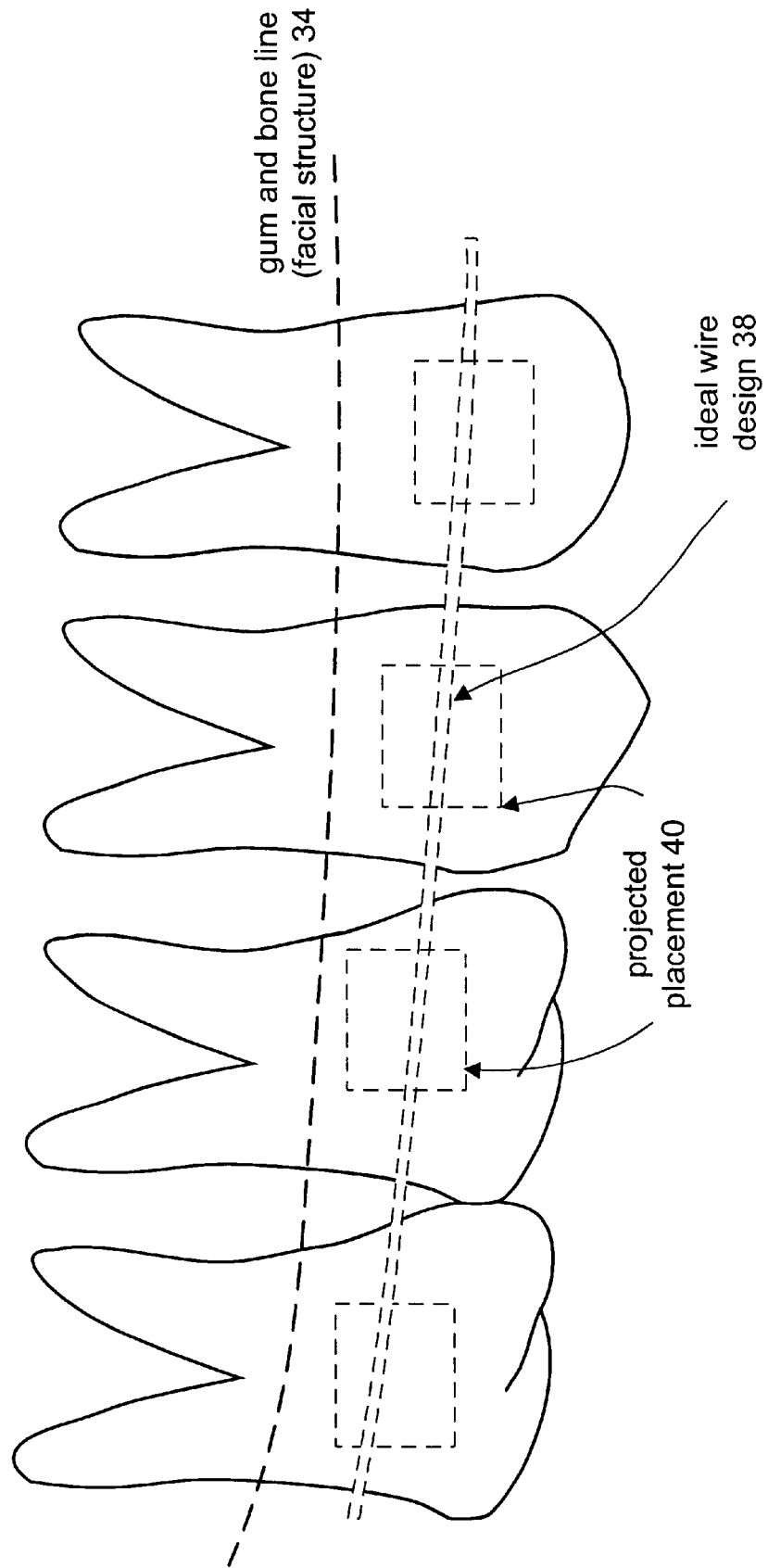
FIG. 3 illustrates a graphical representation of projected bracket placement in accordance with a preferred embodiment of the present invention.

FIG. 3 illustrates an alternative mechanism for accurately placing the brackets. As discussed with reference to FIG. 2, a placement device, such as jig, may be utilized to actually place the brackets on the teeth and then scanned to determine whether the actual positioning is in the desired location. Note that the scanning provides a feedback loop. Further note that the feedback of the actual placement may be achieved by digitizing discrete points on the bracket with ultrasound, light scanning, laser, or any other scanning method. If not, the brackets are repositioned until the desired location is achieved. Alternatively, as shown in FIG. 3, a projection 40 may be projected on the teeth to illustrate the desired location. The scanning tool in the site orthodontic system 12 may include a projector such that the orthodontic structure, (i.e., teeth, gums, etc.), are displayed on monitor 13 enabling the practitioner to monitor the positioning of the brackets in accordance with the projection 40. Thus, the practitioner is provided a feedback system to insure the proper placement of the brackets on the teeth. Note that the projection 40 may include a single projection of the outline of the bracket, or a bull's eye type pattern to center the bracket on the tooth. Further note that a combination of the illustration of FIGS. 2 and 3 may be utilized. For example, the bracket may be positioned in accordance with projection and then subsequently scanned utilizing the illustration of FIG. 2 to verify accurate positioning. Still further note that verification may be done by scanning the patient's orthodontic structure directly, scanning a mold of the patient's orthodontic structure, and/or scanning a stereo-lithography of the patient's orthodontic structure, with the orthodontic appliances printed thereon, as a positive or negative image.

Figure 4:
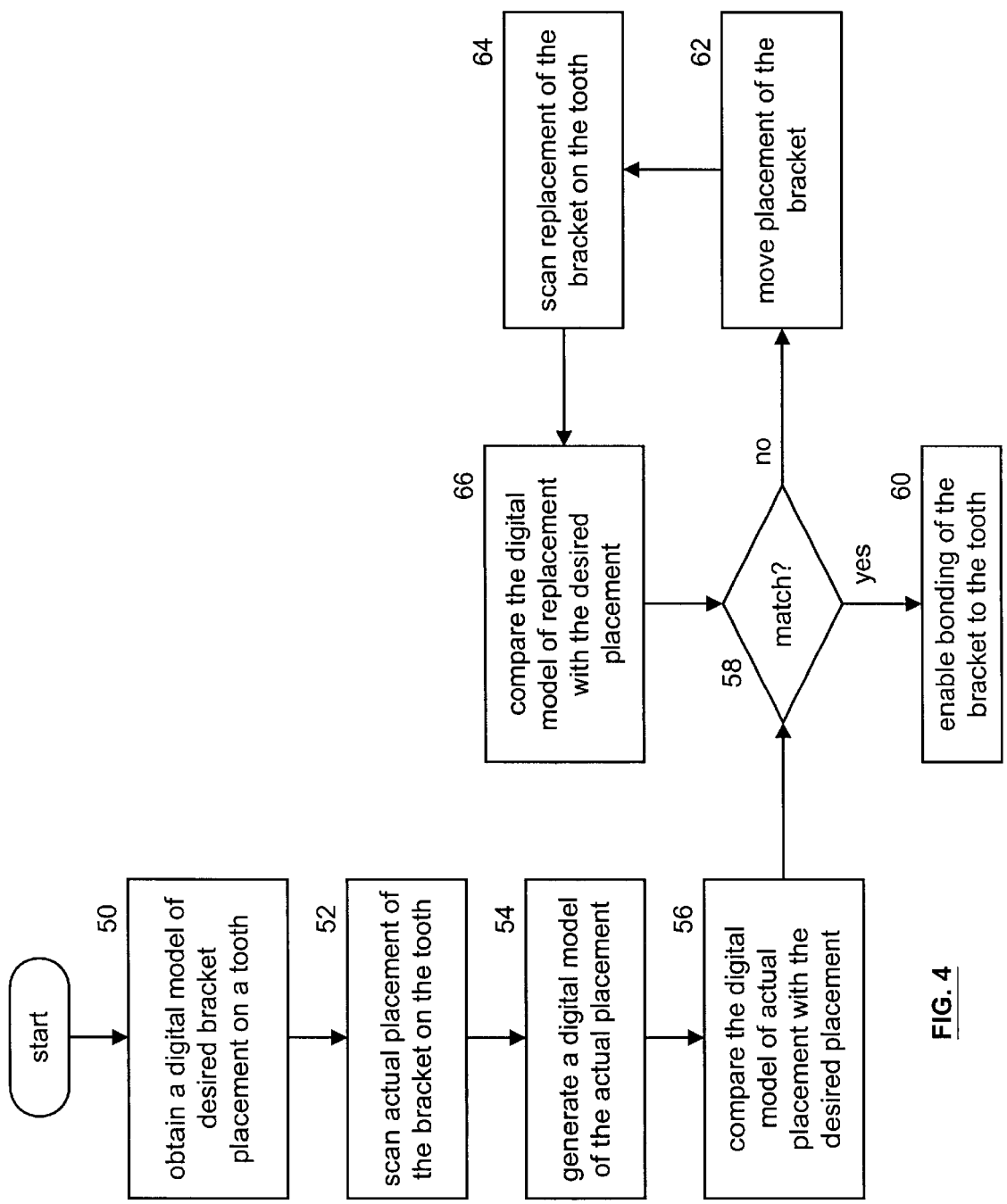
FIG. 4 illustrates a logic diagram of a method for bonding a bracket to a tooth in accordance with a preferred embodiment of the present invention.

FIG. 4 illustrates a logic diagram of a method for bonding a bracket to a tooth by constructing a digital orthodontic template coupled with a validation approach. The process begins at step 50 where a digital model of the desired bracket placement on a tooth is obtained. This is done utilizing the teachings of co-pending patent applications have respective Ser. Nos. of 09/451,609 and 09/451,564. The process then proceeds to step 52 where the actual bracket placement is scanned. Note that the initial bracket may be placed utilizing a robotic placement device in a closed loop scanning process, or utilizing a hand-held placement device in a closed-loop scanning process. If the hand-held placement device is used, the placement process may be enhanced by displaying the scanned images on monitor 13 in a magnified manner.

The process then proceeds to step 54 where a digital model of the actual placement is generated. The process then proceeds to step 56 where the digital model of the actual placement is compared with the digital model of the desired placement. The process then proceeds to step 58 where a determination is made as to whether the actual placement substantially matches the desired placement. A substantial match will depend on the particular type of forced system desired and the accuracy in which the orthodontist wants to practice. Typically, the error (i.e., or a substantial match) will have a vector magnitude variance of less than one millimeter and an angular rotational variance of less than a few degrees. The orthodontist may determine the error based on the patient's needs. Note that the bracket may not be accurately placed for a variety of reasons including, but not limited to, the base being misaligned with respect to the bracket, the bonding agent thickness is incorrect, and/or any imperfections in the manufacture of the bracket.

If the actual placement and desired placement match, the process proceeds to step 60 where the bonding is enabled such that the bracket is permanently adhered to the tooth, where permanently refers to the duration of the patient treatment. Note that the processing steps discussed thus far may be performed on a tooth-by-tooth basis for multiple teeth. Once one tooth has been completed, the process is repeated for other teeth. Further note that the enabling of the bonding may be done by activating a light source to cure a bonding adhesive thereby securing the bracket to the tooth. The bonding adhesive may be cement, and/or any chemical adhesion used by orthodontists for such bonding purposes. As one of average skill in the art will appreciate, multiple teeth may be processed in parallel using the present teachings.

If the actual bracket placement does not substantially match the desired bracket placement the process proceeds to step 62. At step 62 the actual placement of the bracket is moved. The movement of bracket placement may be assisted by providing corrective feedback positioning information utilizing the scanning process. For instance, the scanning process may indicate that the bracket needs to be moved down and to the left by a millimeter and rotated by an angle of 2 degrees, etc. Such a recommendation for repositioning is readily calculable from the digital model of the desired position and the digital model of the current actual placement. Having moved the bracket, the process proceeds to step 64 where the replacement positioning of the bracket is scanned. The process then proceeds to 66 where the digital image of the replacement movement of the bracket is compared with the desired placement. The process then proceeds to step 58. The process will remain in loop 58 through 66 until the actual placement substantially matches the desired placement.

Figure 5:
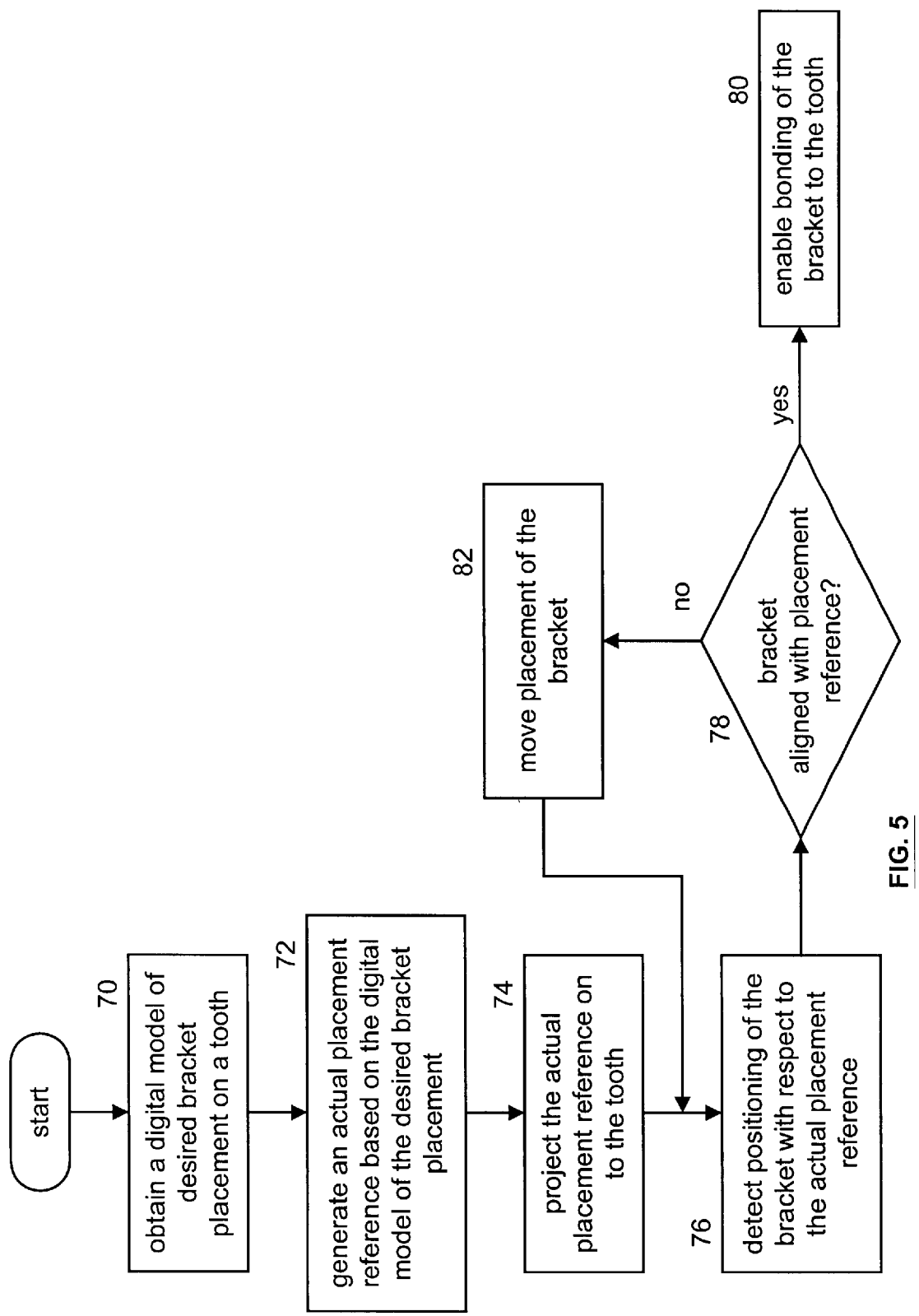
FIG. 5 illustrates a logic diagram of an alternate method for bonding a bracket to a tooth in accordance with another preferred embodiment of the present invention.

FIG. 5 illustrates a logic diagram of an alternate method for bonding a bracket to a tooth. The process begins at step 70 where a digital model of a desired bracket placement on the tooth is obtained. The process then proceeds to step 72 where an actual placement reference is generated based on the digital model of the desired bracket placement. The process then proceeds to step 74 where the actual bracket placement reference is projected onto the tooth. This was illustrated with reference to FIG. 3. The process then proceeds to step 76 where the positioning of the bracket is detected with respect to the actual placement reference. The process then proceeds to step 78 where a determination is made as to whether the bracket is aligned with the placement reference. If so, the process proceeds to step 80 where bonding of the bracket to the tooth is enabled.

If the bracket is not aligned with the placement reference, the process proceeds to step 82. At step 82 the placement of the bracket is moved or the arch wire is changed. The movement may be assisted by providing corrective feedback on positioning based on scanning and displaying the actual placement on a monitor or 3D simulations. The process then proceeds to step 76 and remains in loop 76, 78 and 82 until the bracket is aligned with the referenced position. Note that bracket placement may be verified by simulating whether the brackets line up in three-dimensional space or whether at least some of the brackets line up. Further note that bracket placement, adhesive thickness, adjustment of arch wire, ligation forces, choice of alloy, wire cross-section are factors that may be adjusted singularly or in combination to provide the optimal force system and/or optimal placement in a closed loop system.

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes)

can be simulated to determine appropriate treatment changes. Such compensation in treatment is not possible using prior methods which were based upon assumptions from a single model that the tooth movement would progress in a known manner. Therefore, the prior art methods would specify and a single static treatment based upon this assumption.. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, can be monitored and adjusted as needed by the system in an efficient manner. As such, unexpected tooth movement, such as occurs when a patient does not cooperate, or through biological changes, can be readily controlled.

The preceding discussion has presented a method and apparatus for bonding a bracket to a tooth. By utilizing the teachings of the present invention, orthodontic practice may be enhanced by verifying the accuracy of bracket placement before permanently bonding the bracket to the tooth. As discussed, the more accurate the bracket placement is, the more quickly and effectively orthodontic treatment will be obtained. As one of average skill in the art will appreciate, other embodiments may be derived from the teachings of the present invention without deviating from the scope of the claims.

What is claimed is:

1. A method of bonding of a bracket on to a tooth, the method comprising the steps of:
    a) obtaining a digital representation of at least one of a desired bracket placement on the tooth and a model thereof;
    b) scanning an actual placement of the bracket on the tooth to produce digital information of the actual placement;
    c) generating a digital representation of the actual placement; and
    d) determining whether the digital representation of the desired bracket placement substantially matches the digital representation of the actual placement.

2. The method of claim 1 further comprises repeating steps (a) through (d) for each of a plurality of teeth.

3. The method of claim 1 further comprising:
    when the digital representation of the desired bracket placement does not substantially match the digital representation of the actual placement, moving placement of the bracket;
    determining a replacement of the bracket to obtain a digital representation of the replacement of the bracket;
    comparing the digital representation of the desired bracket placement with the digital representation of the replacement; and
    when the digital representation of the desired bracket placement substantially matches the digital representation of the replacement, bonding the bracket to the tooth.

4. The method of claim 1, wherein the placement further comprises positioning the bracket in a closed loop scanning process utilizing a robotic placement device.

5. The method of claim 1, wherein the placement further comprises positioning the bracket in a closed loop scanning process utilizing a handheld placement device.

6. The method of claim 1, further comprises providing corrective feedback on positioning based on the scanning.

7. The method of claim 1, further comprises displaying the actual placement on a monitor.

8. The method of claim 1, further comprises enabling a light source to cure a bonding adhesive such that the bracket is bonded to the tooth.

9. A method of bonding of a bracket on to a tooth, the method comprises the steps of:
    a) obtaining a digital representation of a desired bracket placement on the tooth;
    b) generating an actual placement reference based on the digital representation of the desired bracket placement;
    c) projecting the actual placement reference on to the tooth; and
    d) detecting positioning of the bracket with respect to the actual placement reference.

10. The method of claim 9, further comprises providing corrective feedback on positioning based on the scanning.

11. The method of claim 9, further comprises displaying the actual placement on a monitor.

12. The method of claim 9, further comprises enabling a light source to cure a bonding adhesive such that the bracket is bonded to the tooth.

13. The method of claim 9, wherein step (a) further comprises:
    scanning a physical model having the bracket placed thereon to obtain a digital representation of the physical model; and
    verifying placement of the bracket based on the digital representation of the physical model and the digital representation of the desired bracket placement on the tooth.

14. An apparatus for bonding of a bracket on to a tooth, the apparatus comprising in combination:
    at least one processing module; and
    memory operably coupled to the at least one processing module, wherein the memory stores operational instructions that cause the at least one processing module to: (a) obtain a digital representation of a desired bracket placement on the tooth; (b) scan actual placement of the bracket on the tooth to produce digital information of the actual placement; (c) generate a digital representation of the actual placement; and (d) compare the digital representation of the desired bracket placement with the digital representation of the actual placement to determine if the desired bracket placement substantially matches the digital representation of the actual placement.

15. The apparatus of claim 14, wherein the memory further comprises operational instructions that cause the at least one processing module to repeat steps (a) through (d) for each of a plurality of teeth.

16. The apparatus of claim 14, wherein the memory further comprises operational instructions that cause the at least one processing module to:
    when the digital representation of the desired bracket placement does not substantially match the digital representation of the actual placement, move placement of the bracket;
    scan a replacement of the bracket to obtain a digital representation of the replacement of the bracket; and
    compare the digital representation of the desired bracket placement with the digital representation of the replacement to determine if the desired bracket placement substantially matches the digital representation of the replacement.

17. The apparatus of claim 14, wherein the placement further comprises positioning the bracket in a closed loop scanning process utilizing a robotic placement device.

18. The apparatus of claim 14, further comprises a handheld placement device for positioning the bracket in a closed loop scanning process.

19. The apparatus of claim 14, wherein the memory further comprises operational instructions that cause the at least one processing module to provide corrective feedback on positioning based on the scanning.

20. The apparatus of claim 14, wherein the memory further comprises operational instructions that cause the at least one processing module to display the actual placement on a monitor.

21. The apparatus of claim 14, wherein the memory further comprises operational instructions that cause the at least one processing module to provide instructions to enable a light source to cure a bonding adhesive such that the bracket is bonded to the tooth.

22. An apparatus for bonding of a bracket on to a tooth, the apparatus comprises:

at least one processing module; and memory operably coupled to the at least one processing module, wherein the memory stores operational instructions that cause the at least one processing module to: (a) obtain a digital representation of desired bracket placement on the tooth; (b) generate an actual placement reference based on the digital representation of the desired bracket placement; (c) project the actual placement reference on to the tooth using a projection system; and (d) detect positioning of the bracket with respect to the actual placement reference to determine if the bracket is substantially aligned with the actual placement reference.

23. The apparatus of claim 22, wherein the memory further comprises operational instructions that cause the at least one processing module to provide corrective feedback on positioning based on the scanning.

24. The apparatus of claim 22, wherein the memory further comprises operational instructions that cause the at least one processing module to display the actual placement on a monitor.

25. The apparatus of claim 22, wherein the memory further comprises operational instructions that cause the at least one processing module to provide instructions to enable a light source to cure a bonding adhesive such that the bracket is bonded to the tooth.

* * * * *